United States Patent [19]

Clark et al.

[11] Patent Number: 5,128,344
[45] Date of Patent: Jul. 7, 1992

[54] SAMPANGINE AND DERIVATIVES USEFUL AS AN ANTIFUNGAL AGENT

[75] Inventors: Alice M. Clark; Charles D. Hufford, both of Oxford; Shihchih Liu, University, all of Miss.; Babajide O. Oguntimein, Adelphi, Md.; John R. Peterson, Oxford, Miss.

[73] Assignee: University of Mississippi, University, Miss.

[21] Appl. No.: 609,610

[22] Filed: Nov. 6, 1990

[51] Int. Cl.$^5$ .................... A61K 31/47; C07D 221/18
[52] U.S. Cl. .................... 514/280; 514/288; 546/66; 546/49
[58] Field of Search ............. 546/66, 49; 514/288, 514/280

[56] References Cited

U.S. PATENT DOCUMENTS 4,080,456  3/1978  Seidelmann et al. ............ 546/66
4,965,272  10/1990 Hufford et al. ............... 514/288

OTHER PUBLICATIONS

Liu, S. et al, "3-Methoxysampangine, a novel antifungal copyrine alkaloid, etc.", CA 113, 37723v (Jul. 1990).
Liu et al, Antimicrobial Agents and Chemotherapy, Apr. 1990, pp. 529-533.
Hufford et al, Journal of Natural Products, vol. 50, No. 5 (1987) pp. 961-964.

Primary Examiner—Richard L. Raymond
Attorney, Agent, or Firm—Morgan & Finnegan

[57] ABSTRACT

A new compound 3-Methoxysampangine and its analogs, compositions thereof, and method of using as an antifungal agent particularly effective against *Candida albicans, Cryptococcus neoformans,* and *Aspergillus fumigatus.*

15 Claims, No Drawings

SAMPANGINE AND DERIVATIVES USEFUL AS AN ANTIFUNGAL AGENT

BRIEF DESCRIPTION OF THE INVENTION

This invention is directed to a new compound, 3-Methoxysampangine, analogs thereof, compositions thereof and a method of providing effective protection against pathological fungal conditions in mammals particularly those caused by *Candida albicans, Aspergillus fumigatus,* and *Cryptococcus neoformans*. The novel compound and compositions of the invention provide in one case a simple, practical readily extracted drug occurring naturally in the root bark of the West African tree, *Cleistopholis patens* (Benth) Engl. and Diels (Annonaceae). The compound of the invention may also be synthesized using known techniques.

The present invention relates to new compounds and an antifungal composition consisting essentially of compounds wherein the compounds are of the formula:

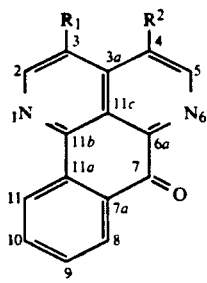

wherein $R_1$ is selected from the group consisting of H and an alkoxy group having 1-6 carbon atoms; $R_2$ is selected from the group consisting of H, Br, Cl, F, I and an alkoxy group having 1-6 carbon atoms when $R_1$ is H; and wherein $R_1$ is H, a benzo group at the 4-5 position. The composition contains the compounds in a therapeutically-effective concentration and a non-toxic, pharmaceutically-acceptable carrier.

SUMMARY AND BACKGROUND OF THE INVENTION

The need for new, more effective, and less toxic antifungal antibiotics for the treatment of disseminated mycotic infections is urgent in view of the significant toxicities and failure rates of the currently available systemic antifungal agents. The problem has become particularly relevant in view of the fact that opportunistic disseminated mycoses is a common complication of Acquired Immune Deficiency Syndrome (AIDS). The discovery of new antibiotics has in the past successfully relied primarily upon the isolation of such agents from natural sources. The principal advantage of this approach over chemical synthesis or modification of existing agents is the probability of discovering new prototype drugs with quite different chemical structures and, therefore, dissimilar toxicities and cross-resistance with present drug therapies.

The discovery and extraction of an antifungal alkaloid eupolauridine from the stem and root bark of the tree *Cleistopholis patens* (Benth) Engl. and Diels (Annonaceae) and useful against *Candida albicans* is the subject of U.S. Pat. No. 4,965,272. The discovery of eupolauridine from the ethanolic extract of the root bark of the tree which is found throughout West Africa and its possibly remarkable anticandidal properties was reported in the Journal of Natural Products, Vol. 50, No. 5, pp. 961-964, Sep.–Oct. 1987 by Hufford et al. Subsequent to the discovery of eupolauridine in the ethanolic extract and its unexpected antifungal properties, the ethanolic extract was subjected to further examination using different bioassay techniques which resulted in the unexpected discovery of a new compound, 3-Methoxysampangine, which exhibits remarkable antifungal properties against *Candida albicans, Aspergillus fumigatus,* and *Cryptococcus neoformans*. The invention is the new compound 3-Methoxysampangine, analogs thereof, compositions thereof, and the method of treatment of pathological conditions caused by fungal organisms comprising administering the compound in a therapeutically-effective concentration in a non-toxic pharmaceutically-acceptable carrier.

Administration of the compound may be by any of the conventional routes of administration, for example, oral, intramuscular, intravenous, or rectally. In the preferred embodiment, the compound is administered in combination with a pharmaceutically-acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include water, edible oils, e.g. peanut and corn.

When administered in solid form, the compound and diluent carrier may be in the form of tablets, capsules, powders, lozenges, suppositories prepared by any of the well known methods. When given as a liquid preparation, the mixture of active compound and liquid diluent carrier may be in the form of a suspension administered as such. The compound is administered in a non-toxic dosage concentration sufficient to inhibit the growth and/or destroy the *Candida albicans, Aspergillus fumigatus* and *Cryptococcus neoformans* organisms. The actual dosage unit will be determined by such generally recognized factors as body weight of the patient and/or severity and type of pathological condition the patient might be suffering with prior to becoming infected with any of the fungal organisms. With these considerations in mind, the dosage unit for a particular patient can be readily determined by the medical practitioner in accordance with the techniques known in the medical arts.

DETAILED DESCRIPTION OF THE INVENTION

The dried ground root bark of *Cleistopholis patens* was percolated initially with n-hexane followed by percolation with 95% ethanol, followed by percolation with hot ethanol. The ethanolic extracts were then combined and subjected to bioassay-directed fractionation by first partitioning between aqueous chloroform followed by aqueous ethyl acetate. The chloroform and ethyl acetate fractions were combined and the combined organic fraction chromatographed over silica gel using chloroform and gradually increasing percentages of methyl alcohol in chloroform as eluents. The methyl alcohol-chloroform fractions were further purified by chromatography over neutral alumina using mixtures of ethyl acetate-n-hexane as eluting solvents.

The novel compound of the invention was obtained as yellow needles having a melting point of 213°-215°. The needles display a pink fluorescence under long wavelength ultraviolet (UV) irradiation on a silica gel thin layer chromatography (TLC) plate. The molecular formula of the compound determined by electron impact mass spectroscopy (EI-MS) showed a molecular ion peak at m/z 262 corresponding to the molecular formula $C_{16}H_{10}N_2O_2$ which formula was confirmed by high resolution mass spectroscopy (HR-MS). The molecular formula derived from the high resolution mass spectrum indicated the presence of a condensed ring system. This was verified by the UV spectrum which showed bands at λmax 309, 332 and 409 nm characteristic of a highly conjugated oxoalkaloid. In the proton nuclear magnetic resonance ($^1$H-NMR) spectrum, four of the seven aromatic protons comprised an ABMX system characteristic of a 1,2-disubstituted benzene nucleus. Two pairs of aromatic doublets coupled to each other (δ9.13 and 8.21) could be assigned to H-2 and H-3 of a pyridine ring. The only remaining signals in the $^1$H NMR were one aromatic proton, resonating as a singlet (δ 8.36) and a three-proton singlet for an aromatic methoxyl at δ 4.18. The $^{13}$C-NMR spectral data revealed sixteen signals as one methoxyl, seven methines and eight quaternary carbons. Based on the $^1$H and $^{13}$C-NMR spectral data, the methoxyl group could be located at either carbons 2, 3, 4, or 5. The location of the methoxyl group at C-3 was established by unambiguous assignment of all of the carbon signals of use of two dimensional nuclear magnetic resonance (2D-NMR) techniques. The structural formula of 3-methoxysampangine is as follows:

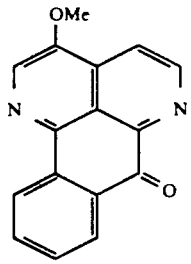

The generic name for the compound is 3-Methoxysampangine. The antifungal activity of the compound was determined by in vitro evaluation against *Candida albicans* NIH B311, *Cryptococcus neoformans* ATCC 32264, and *Aspergillus fumigatus* ATCC 26934 using the known agar-well diffusion assay techniques with the following modifications.

*Candida albicans* NIH B311 used to induce experimental disseminated candidiasis was used for the initial qualitative evaluation of anticandidal activity. The organism was grown in Sabouraud-dextrose broth (SDB) for 24 hours at 37°, at which time the cells were harvested by centrifugation at (4°, 2000 rpm, 3 min.). After centrifugation, the cells were washed and suspended in sterile 0.9% saline to give a final concentration of $10^6$ colony forming units (CFU) per ml (adjusted using a hemocytometer). Inocula of *Cryptococcus neoformans* and *Aspergillus fumigatus* were prepared by suspension of the surface growth of stock agar slants in sterile $H_2O$. Culture plates (15×100 mm) for the qualitative assay were prepared from 25 ml of Sabouraud-dextrose agar for *Candida albicans*, and Mycophil TM agar for *Cryptococcus neoformans* and *Aspergillus fumigatus*. Using sterile cotton swabs, the plates were streaked with the suspension of appropriate test organism. Cylindrical plugs were removed from the agar plates by means of sterile cork borer to produce wells with a diameter of approximately 11 mm. To the well was added 100 μl of solution or suspension of an extract, fraction, or pure compound. Crude extracts and fractions were tested at a concentration of 20 mg/ml, whereas pure compounds were tested at 1 mg/ml. When solvents other than water, ethanol, methanol, dimethylsulfoxide (DMSO), dimethylformamide (DMF), or acetone were required to dissolve extracts or compounds, solvent blanks were included. Antifungal activity was recorded as the width (in mm) of the zone of inhibition, measured from the edge of the agar well to the edge of the zone, following incubation of the plates for 24 hours (37° for *Candida albicans*, 30° for *Aspergillus fumigatus* and 26° for *Cryptococcus neoformans*). The antifungal agents amphotericin B and ketoconazole were included as positive controls in each assay.

The method used to determine the minimum inhibitory concentration (MIC) was the twofold serial broth dilution assay in one or more of the following broth media: yeast nitrogen broth, Mycophil TM broth and Saboraud-dextrose broth (SDB). The inoculum for the MIC determination was prepared as described above for the qualitative evaluation. Using a calibrated sterile wire loop, each tube was inoculated with 10 μl of the suspension. The MIC value was taken as the lowest concentration of compound that inhibited the growth of the test organisms after an appropriate incubation period (37° for 24 hours for *Candida albicans*; 30° for 48 hours for *Aspergillus fumigatus*; 26° for 48 hours for *Cryptococcus neoformans*). The antifungal agent amphotericin B was included as positive control in each assay. The results of the test utilizing 3-Methoxysampangine, Sampangine, 4-Bromosampangine, and 4-Methoxysampangine demonstrating significant antifungal activity against both yeasts, *Candida albicans* and *Cryptococcus neoformans* and the filamentous fungus, *Aspergillus fumigatus* are illustrated in Table I. The data in Table I clearly demonstrate that the compound and its analogs exhibit in vitro activity

TABLE I

| Sample Name | Media[a] | MIC (μg/mL)[b] Ca B311[c] | Cn[c] | Af[c] |
|---|---|---|---|---|
| Sampangine | YNB (original) | 1.56 | <0.005 | NT |
| Sampangine | YNB | 0.78 | <0.20 | NT |
| Sampangine | SDB | 6.25 | <0.20 | NT |
| Sampangine | MYCO | 12.5 | 0.78 | 1.56 |
| 3-Methoxysampangine | SDB | 3.12 | 0.20 | 3.12 |
| 4-Bromosampangine | YNB | 12.5 | <0.20 | NT |
| 4-Bromosampangine | SDB | 25 | 0.39 | NT |
| 4-Bromosampangine | MYCO | 25 | <0.20 | 50 |
| 4-Methoxysampangine | YNB | 3.12 | 12.5 | NT |
| 4-Methoxysampangine | SDB | 100 | 3.12 | NT |
| 4-Methoxysampangine | MYCO | 100 | 1.56 | NT |
| Benzo[4,5]sampangine | YNB | 3.12 | 1.56 | NT |
| Benzo[4,5]sampangine | SDB | 1.56 | <0.20 | NT |
| Benzo[4,5]sampangine | MYCO | 50 | <0.20 | 0.39 |
| Amphotericin B | MYCO | 0.20 | 0.20 | 3.12 |

[a]YNB = Yeast nitrogen base broth. SDB = Sabouraud dextrose broth. MYCO = Mycophil TM (BBL) broth.
[b]MIC = Minimum inhibitory concentration. NT = not tested.
[c]Ca B311 = *Candida albicans*. Cn = *Cryptococcus neoformans*. Af = *Aspergillus fumigatus*.

against one or more fungal pathogens at potencies comparable to, and in many cases better than, a current drug of choice, amphotericin B.

The compound and its analogs were synthesized according to the method shown in Scheme I. Cleistopholine (3) was obtained in a single step (57% yield) through the hetero Diels-Alder reaction of 2-bromo- 1,4-naphthoquinone (1) with (E)-2-butenal N,N-dimethylhydrazone (2), followed by in situ elimination of dimethylammonium bromide. The condensation of cleistopholine with dimethylformamide dimethyl acetal provided sampangine (4) in 79% yield. Electrophilic bromination of sampangine with pyridinium bromide perbromide or bromine/pyridine complex delivered exclusively 4-bromosampangine (5, 64%), rather than the anticipated 3-bromo analog. Methanolysis of 4-bromosampangine subsequently led to 4-methoxysampangine (6) in 55% yield. The NMR spectral data for sampangine and 4-methoxysampangine are compared with that for 3-methoxysampangine in Tables II and III. These assignments are based on a careful analysis of the $^1$H, attached proton test (APT), correlated spectroscopy (COSY), and short and long range (J=5 and 10 Hz) heterocorrelated (HETCOR) NMR spectra for each compound. The unambiguous C-7 carbonyl resonance allows for a clear recognition of certain key atoms through HETCOR three-bond connections (e.g. H-8, C-10, etc.) and thence the remaining atoms by correlation with the other spectra. Consistent with these assignments are significant chemical shift changes for C-4, C-5, C-6a, H-3 and H-5 of 4-methoxysampangine and C-2, C-3, C-11b, H-2 and H-4 of 3-methoxysampangine relative to sampangine.

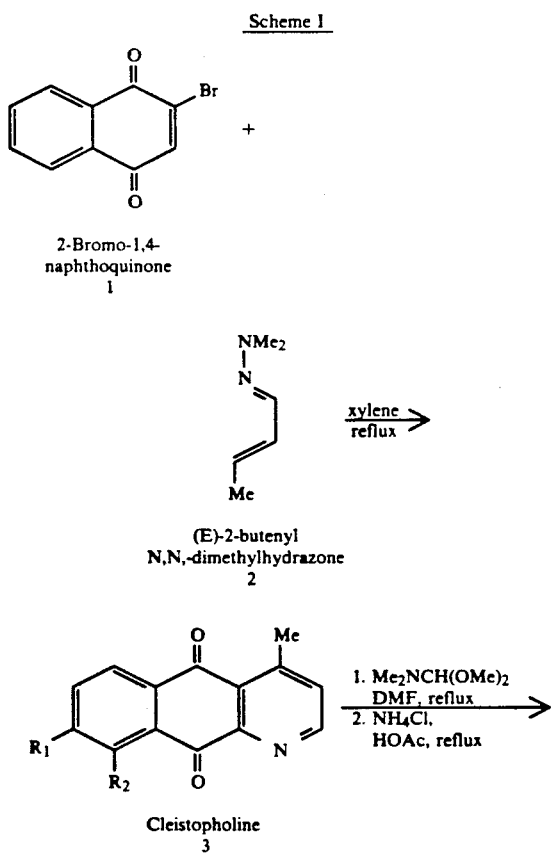

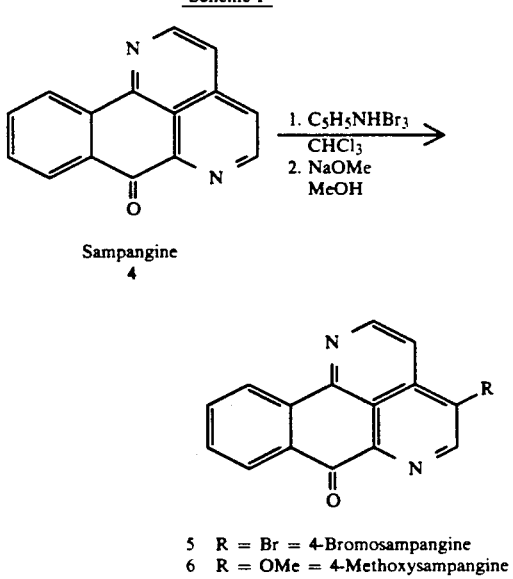

5  R = Br  = 4-Bromosampangine
6  R = OMe = 4-Methoxysampangine

EXAMPLE I

Preparation of 2-Bromo-1,4-naphthoquinone (1). A 3-L, three-necked, round-bottomed flask fitted with a mechanical stirrer, a 500-mL addition funnel and a thermometer was changed with glacial acetic acid (500 mL), water (1000 mL) and N-bromosuccinimide (71.2 g, 0.40 mol). The mixture was warmed to 45° C. during which time a yellow solution was obtained. An acetic acid (500 mL) solution of 1-naphthol (14.4 g, 0.10 mol) was then added dropwise over a period of 75 min so as to give a red solution, the latter of which was stirred an additional 30 min at 45° C. before cooling to room temperature. The resulting mixture was diluted with water (1500 mL) and extracted with methylene chloride (6×400 mL). The combined organic extracts were in turn washed with water (4×400 mL) and saturated sodium bicarbonate solution (4 ×300 mL). Rotary evaporation of the solvent following drying over magnesium sulfate yielded a yellow solid that was recrystallized from 95% ethanol to yield pure 2-Bromo-1,4-naphthoquinone (18.50 g, 78%); mp 130.5°-132° C. (lit. mp 131°-132° C.). IR(KBr) 3050, 1675, 1655, 1585, 1570, 1330, 1310, 1295, 1270, 1245, 1220, 1120, 1060, 910, 890, 820, 790, 775, 670, 665 cm$^{-1}$; $^1$H NMR (CDCl$_3$) δ 8.21-8.14 (m, 1 H), 8.11-8.05 (m, 1 H), 7.80-7.73 (m, 2 H), 7.52 (s, 1 H); $^{13}$C NMR (CDCl$_3$) 182.4 (0), 177.8 (0), 140.3 (1), 140.1 (0), 134.4 (1), 134.1 (1), 131.7 (0), 130.9 (0), 127.8 (1), 126.9 (1) ppm.

EXAMPLE II

Preparation of (E)-2-Butenal N,N-Dimethylhydrazone (2). A 250-mL, round-bottomed flask equipped with a 60-mL addition funnel was charged with crotonaldehyde (74.7 mL, 0.90 mol) and cooled in an ice-water bath. 1,1-Dimethylhydrazine (75.3 mL, 0.99 mol) was then added dropwise to the cold aldehyde over a period of 15 min. The layers were separated after allowing the reaction to stir at ambient temperature for 45 min. The organic layer was dried over calcium chloride, decanted, and distilled through a Vigreaux column. Collection of the fraction boiling at 53°-58° C., 15-18 mm Hg (water aspirator) gave 58.8 g (58%) of pure (E)

-2-Butenal N,N-dimethylhydrazone. $^1$NMR (CDCl$_3$) δ 6.98 (d, J=8.9 Hz, 1 H), 6.18 (ddq, J=15.5, 8.9, 1.7 Hz, 1 H), 5.78 (dq, J=15.5, 6.8 Hz, 1 H), 2.78 (s, 6 H), 1.78 (dd, J=6.8, 1.7 Hz, 3 H).

EXAMPLE III

Preparation of Cleistopholine (4). (E)-2-Butenal N,N-dimethylhydrazone, (3.70 g, 0.033 mol) in dry xylene (10 mL, Fisher) was added to a xylene solution (50 mL) of 2-bromo-1,4-naphthoquinone, (6.00 g, 0.025 mol) in a 200-mL, round-bottomed flask fitted with a condensor. The dark mixture was then heated at reflux for 6 h under a nitrogen atmosphere before decanting the solution into a 500-mL separatory funnel. The solids coating the wall of the flask were washed thoroughly with ethyl acetate (6×25 mL) and these washings added to the separatory funnel. The combined organic solutions were extracted with 2N sulfuric acid solution (1×100 mL followed by 2×75 mL). The acid layers were then combined, chilled in ice, and made basic (~pH 10 test paper) with sodium hydroxide before extracting with ethyl acetate (4×100 mL). The latter organic layers were dried over potassium carbonate and concentrated to dryness on a rotary evaporator. This material was applied to a 4×70 cm column of Silica gel (Merck 230-400 mesh) and the product eluted with ethyl acetate. Concentration of the appropriate column fractions yielded pure cleistopholine (3.20 g, 57%); mp 202°-204° C. (lit. mp 198°-201° C.). IR(KBr) 1680, 1660, 1590, 1300, 980, 720 cm$^{-1}$; $^1$H NMR (CDCl$_3$) δ 8.86 (d, J=4.9 Hz, 1 H), 8.34-8.30 (m, 1 H), 8.24-8.19 (m, 1 H), 7.82-7.76 (m, 2 H), 7.47 (dd,J=4.9, 0.7 Hz, 1 H), 2.88 (br s, 3 H); $^{13}$C NMR (CDCl$_3$) 184.7 (0), 181.9 (0), 153.4 (1), 151.5 (0), 150.0 (0), 134.5 (1), 134.1 (1), 133.8 (0), 132.5 (0), 131.2 (1), 129.1 (0), 127.3 (1), 127.1 (1), 2.28 (3) ppm.

EXAMPLE IV

Preparation of Sampangine (4). Dimethylformamide dimethyl acetal (1.50 mL, 11.34 mmol, Aldrich) was added to a solution of cleistopholine, (1.95 g, 8.73 mmol) in dimethylformamide (5 mL). The mixture was then heated for 30 min by submerging

TABLE II $^1$H NMR DATA FOR SAMPANGINE, 4-METHOXYSAMPANGINE AND 3-METHOXYSAMPANGINE.

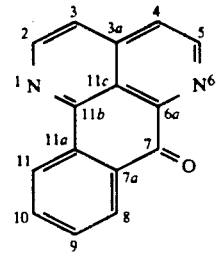

| Position | sampangine (4) | Chemical Shift, ppm (CDCl$_3$) 4-methoxysampangine (6) | 3-methoxysampangine |
|---|---|---|---|
| 2 | 8.88(d, J=5.8Hz, 1H) | 8.89(d, J=5.8Hz, 1H) | 8.36(s, 1H) |
| 3 | 7.71(d, J=5.8Hz, 1H) | 8.00(d, J=5.8Hz, 1H) | — |
| 3a | — | — | — |
| 4 | 7.92(d, J=5.5Hz, 1H) | — | 8.21(d, J=5.4Hz, 1H) |
| 5 | 9.13(d, J=5.5Hz, 1H) | 8.66(s, 1H) | 9.13(d, J=5.4Hz, 1H) |
| 6a | — | — | — |
| 7 | — | — | — |
| 7a | — | — | — |
| 8 | 8.46(dd, J=7.8, 1.2Hz, 1H) | 8.49(dd, J=7.9, 1.2Hz, 1H) | 8.43(dd, J=7.8, 1.2Hz, 1H) |
| 9 | 7.69(ddd, J=7.8, 7.8, 1.2Hz, 1H) | 7.69(ddd, J=7.9, 7.9, 1.2Hz, 1H) | 7.61(ddd, J=7.8, 7.8, 1.2Hz, 1H) |
| 10 | 7.83(ddd, J=7.8, 7.8, 1.2Hz, 1H) | 7.82(ddd, J=7.9, 7.9, 1.2Hz, 1H) | 7.78(ddd, J=7.8, 7.8, 1.2Hz, 1H) |
| 11 | 8.82(dd, J=7.8, 1.2, 1H) | 8.85(dd, J=7.9, 1.2Hz, 1H) | 8.65(dd, J=7.8, 1.2 Hz, 1H) |
| 11a | — | — | — |
| 11b | — | — | — |
| 11c | — | — | — |
| OCH$_3$ | — | 4.25(s, 3H) | 4.18(s, 3H) |

TABLE III $^{13}$C NMR DATA FOR SAMPANGINE, 4-METHOXYSAMPANGINE AND 3-METHOXYSAMPANGINE.

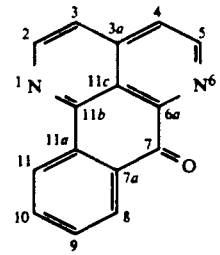

| Position | sampangine (4) | Chemical Shift (CDCl$_3$) 4-methoxysampangine (6) | 3-methoxy-sampangine |
|---|---|---|---|
| 2 | 147.1 (1) | 146.6 (1) | 126.8 (1) |
| 3 | 118.9 (1) | 114.3 (1) | 149.9 (0) |
| 3a | 138.3 (0) | 130.3 (0) | 131.8 (0) |
| 4 | 123.2 (1) | 152.7 (0) | 118.8 (1) |
| 5 | 148.2 (1) | 128.9 (1) | 148.0 (1) |
| 6a | 147.5 (0) | 141.0 (0) | 147.2 (0) |
| 7 | 181.5 (0) | 181.1 (0) | 182.0 (0) |
| 7a | 132.0 (0) | 132.8 (0) | 131.5 (0) |
| 8 | 128.1 (1) | 128.4 (1) | 128.5 (1) |
| 9 | 131.1 (1) | 131.2 (1) | 130.2 (1) |

TABLE III-continued

13C NMR DATA FOR SAMPANGINE, 4-METHOXYSAMPANGINE AND 3-METHOXYSAMPANGINE.

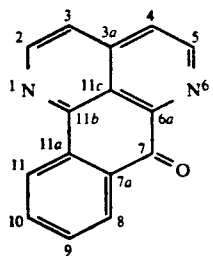

| Position | sampangine (4) | Chemical Shift (CDCl$_3$) 4-methoxysampangine (6) | 3-methoxy-sampangine |
|---|---|---|---|
| 10 | 134.4 (1) | 134.2 (1) | 134.6 (1) |
| 11 | 125.1 (1) | 125.3 (1) | 124.6 (1) |
| 11a | 135.0 (0) | 135.6 (0) | 135.7 (0) |
| 11b | 150.7 (0) | 150.4 (0) | 143.2 (0) |
| 11c | 119.3 (0) | 120.0 (0) | 119.7 (0) |
| OCH$_3$ | — | 56.9 (3) | 56.6 (3) | the reaction vessel into an oil bath preheated to 120° C. At this point, ammonium chloride (4.5 g) and glacial acetic acid (15 mL) were added to the reaction and the heating (120° C.) continued for an additional 30 min. After allowing to cool, the reaction was poured onto water (200 mL) and partitioned with methylene chloride (5×100 mL). The combined organic phases were washed with saturated sodium bicarbonate solution (3×100 mL), water (3×100 mL), dried over potassium carbonate, and concentrated to dryness. The residual dark brown solids were chromatographed on silica gel (4×70 cm column, Merck 230–400 mesh) while eluting with ethyl acetate. Concentration of the appropriate column fractions provided pure sampangine (1.60 g, 79%), mp 220–222 (lit. mp 216°-218° C.). IR 1670, 1615, 1590, 1400, 1380, 1320, 1275, 1225, 760, 725 cm$^{-1}$; $^1$H and $^{13}$C NMR (see Tables II and III).

EXAMPLE V

Preparation of 4-Bromosampangine (5). A mixture of pyridinium bromide perbromide (390 mg, 1.2 mmol) and sampangine, (232 mg, 1.0 mmol) in chloroform (12 mL) was heated at reflux for 15 h. Saturated sodium bicarbonate solution (100 mL) was added to the cooled reaction and the mixture stirred vigorously for 30 min. The two layers were separated and the aqueous phase extracted with chloroform (2×30 mL). The combined organic layers were dried over potassium carbonate and concentrated to dryness. The residual solid was applied to a 2×40 cm column of silica gel (Merck 230–400 mesh) and the pure product (200 mg, 64%) eluted with chloroform, mp 180° C. dec. IR (KBr) 1670, 1590, 1400, 1320, 1310, 1275, 1230, 980, 790, 755, 720 cm$^{-1}$; $^1$H NMR (CDCl$_3$) δ 9.28 (s, 1 H), 8.99 (d, J=5.9 Hz, 1 H), 8.85 (dd, J=7.9, 1.4 Hz, 1 H), 8.46 (dd, J=7.9, 1.4 Hz, 1 H), 7.96 (d, J=5.9 Hz, 1 H), 7.86 (ddd, J=7.7, 7.9, 1.4 Hz, 1 H), 7.72 (ddd, J=7.9, 7.9, 1.4 Hz, 1 H); $^{13}$C NMR (CDCl$_3$) 181.6 (0), 151.7 (0), 150.2 (1), 148.6 (1), 146.7 (0), 138.6 (0), 135.1 (0), 135.0 (1), 132.3 (0), 131.8 (1), 128.7 (1), 125.8 (1), 123.7 (0), 120.5 (0), 118.3 (1) ppm; HR MS calc. for C$_{15}$H$_7$BrN$_2$O 309.9741, found 309.9747.

EXAMPLE VI

Preparation of 4-Methoxysampangine (6). A dry methanol (6 mL) solution of sodium methoxide (80 mg, 1.48 mmol) and 4-bromosampangine, (80 mg, 0.26 mmol) was heated to reflux for 20 h. The cooled solution was transferred to a separatory funnel, diluted with chloroform (50 mL), and washed with water (2×60 mL). The chloroform layer was subsequently dried over potassium carbonate and concentrated to dryness. TLC analysis of the residue (silica gel, ethyl acetate eluant) revealed only one spot (R$_f$=0.15) that was substantially more polar than 4-methoxysampangine. Chromatography of this residue on silica gel (1×25 cm column, Merck 230–400 mesh) while eluting with ethyl acetate-methanol (4:1) provided pure 4-methoxysampangine (37 mg, 55%), mp 258° C. dec. IR (KBr) 1670, 1595, 1570, 1500, 1405, 1375, 1320, 1295, 1240, 1100, 1040, 1030, 985, 920, 790, 720, 615 cm$^{-1}$; $^1$H and $^{13}$C NMR (see Tables II and III).

EXAMPLE VII

Preparation of Benzo[4,5]sampangine (9). As illustrated in Scheme II, a suspension of 4.47 g (0.03 mol) of 1,4-naphthoquinone (7) in 600 ml of absolute ethanol, containing 3.37 g (0.03 mol) of 1-aminoacetophenone (8) and 1.66 g (0.003 mol) of cerium trichloride heptahydrate was warmed to dissolve, then allowed to stand at room temperature and a steady current of air was continuously blown into the reaction mixture for 24 h. A red precipitate was formed and collected by filtration, then washed with a small amount of absolute ethanol. The filtrate was repeated above procedure twice, and a total of 7.26 g (60.4%) of 2-[o-acetyl]-anilino-1,4-naphthoquinone (9) was obtained as red needles, mp. 177°-179° C. EIMS m/z 291 (M+), $^1$H-nmr, δ(CDCl$_3$) 2.66 (3H, s), 6.99 (1H, s) 7.06 (1H, d, J=9.0 Hz), 7.14 (1H, ddd, J=6.0, 6.0, 1.0 Hz), 7.55 (1H, ddd, J=9.0, 6.0, 1.0 Hz), 7.65 (1H, ddd, J=8.0, 8.0, 1.5 Hz), 7.73(1H, ddd, J=8.0,8.0, 1.5 Hz), 7.93 (1H, dd, J=6.0, 1.0 Hz), 8.05 (1H, dd, J=9.0, 1.0 Hz), 8.13 (1H, dd, J=9.0, 1.0 Hz).

Scheme II

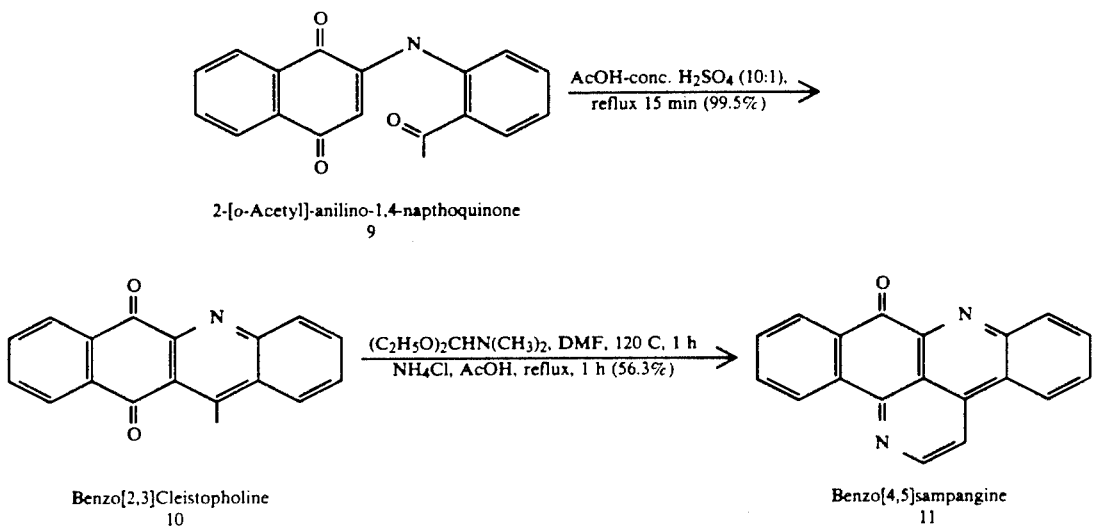

-continued
Scheme II

2-[o-Acetyl]-anilino-1,4-napthoquinone
9

Benzo[2,3]Cleistopholine
10

Benzo[4,5]sampangine
11

To a cold, stirred suspension of 4 g (15.7 m mols) of 2-[o-acetyl]-anilino-1,4-naphthoquinone (9) in 13.2 mL of glacial acetic acid was slowly added 13.2 ml of concentrated $H_2SO_4$. The reaction mixture was then gently refluxed for 15 min., cooled, and poured into 2 liters of ice-$H_2O$. The yellow precipitate was collected and washed with a small amount of ice cold $H_2O$ to give 3.23 g (99.5%) of dirty greenish yellow fine needles of Benzo[2,3]cleistopholine (10) mp. 237°-239° (d). EIMS M/z 273($M^+$), IR$\upsilon$ $_{max}$(KBr) 1680, 1655, 1590, 1495, 1375, 1260, 1080, 943, 770, 720 $cm^{-1}$. $^1H$-nmr, $\delta$(CDCl$_3$) 3.22(3H, s, CH$_3$-13),7.69(1H, ddd,J=6.7, 6.7, 1.3 Hz), 7.70(1H, m), 7.78(1H, m), 7.84(1H, ddd, J=6.7, 6.7, 1.3 Hz), 8.25(1H, dd, J=6.0, 2.5 Hz), 8.29(1H, brd, J=6.7 Hz), 8.34(1H, dd, J=6.0, 2.5 Hz), 8.39(1H, brd, J=6.7 Hz).

A suspension of 2.38 g (8.73 m mol) of Benzo[2,3]-cleistopholine in 3 ml of DMF and 1.67 g of dimethyl formamide-diethylacetal was stirred under $N_2$ and heated at 120° C. for 1 h. The reaction mixture was cooled and 15 ml of glacial acetic acid and 4.5 g of NH$_4$Cl was added carefully and the reaction mixture was refluxed for another hour. Water (300 ml) was added to the reaction mixture, followed by extraction with CH$_2$Cl$_2$ (150 ml×4). The total organic layer was washed with 150 ml of saturated NaHCO$_3$ solution, then with 150 ml of H$_2$O, and dried over anhydrous K$_2$CO$_3$. After removal of solvent, the resulting residue was chromatographed over silica gel (400 g) and eluted with ethyl acetate to give 1.824 (56.3%) of Benzo[4,5-]sampangine (11), as bright yellow needles, mp. 260°-262° C. EIMS m/z 282($M^+$), IR$\upsilon$ $_{max}$(KBr) 1680, 1590, 1442, 1390, 1300, 1262, 1060, 950, 767, 740 $cm^{-1}$. $^1H$ and $^{13}C$ NMR (see Table IV).

TABLE IV $^1H$ AND $^{13}C$ NMR DATA FOR BENZO[4,5]SAMPANGINE

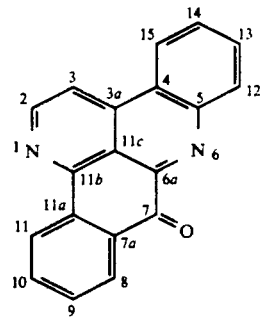

| Position | $^1H$ NMR | $^{13}C$ NMR |
| --- | --- | --- |
| 2 | 8.97(d, J=5.7Hz, 1H) | 148.9 (1) |
| 3 | 8.30 (d, J=5.7Hz, 1H) | 115.5 (1) |
| 3a | — | 137.8 (0) |
| 4 | — | 123.5 (0) |
| 5 | — | 145.8 (0) |
| 6a | — | 146.0 (0) |
| 7 | — | 182.2 (0) |
| 7a | — | 132.5 (0) |
| 8 | 8.44(dd, J=7.8, 1.0Hz, 1H) | 128.7 (1) |
| 9 | 7.66(ddd, J=7.8, 7.4, 1.0Hz, 1H) | 131.2 (1) |
| 10 | 7.80(ddd, J=7.8, 7.4, 1.0Hz, 1H) | 134.9 (1) |
| 11 | 8.79(dd, J=7.8, 1.0Hz, 1H) | 125.8 (1) |
| 11a | — | 136.1 (0) |
| 11b | — | 150.5 (0) |
| 11c | — | 117.0 (0) |
| 12 | 8.55(dd, J=7.1, 1.4Hz, 1H) | 133.1 (1) |
| 13 | 7.93(ddd, J=7.1, 7.0, 1.4Hz, 1H) | 131.6 (1) |
| 14 | 7.84(ddd, J=7.1, 7.0, 1.4Hz, 1H) | 130.3 (1) |
| 15 | 8.55(dd, J=7.1, 1.4Hz, 1H) | 122.9 (1) |

We claim:
1. An antifungal composition consisting essentially of a compound having the formula

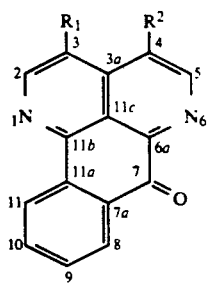

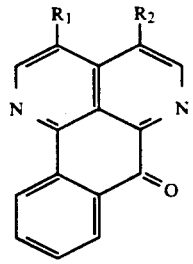

wherein $R_1$ is selected from the group consisting of H and an alkoxy group having 1-6 carbon atoms; $R_2$ is selected from the group consisting of H, Br, Cl, F, I and an alkoxy group having 1-6 carbon atoms when $R_1$ is H; and wherein $R_1$ is H and at the 4-5 position a benzo group, in a therapeutically-effective concentration and a non-toxic, pharmaceutically-acceptable carrier.

2. The antifungal composition of claim 1 wherein said compound is Sampangine.

3. The antifungal composition of claim 1 wherin said compound is 3-Methoxysampangine.

4. The antifungal composition of claim 1 wherein said compound is 4-Methoxysampangine.

5. The antifungal composition of claim 1 wherein said compound is 4-Bromosampangine.

6. A method for preventing pathological conditions in mammals brought about by the presence of a fungal organism comprising administering to said mammals in a therapeutically-effective concentration, a composition consisting essentially of a compound having the formula wherein $R_1$ is selected from the group consisting of H and an alkoxy group having 1-6 carbon atoms, and wherein $R_2$ is selected from a group consisting of H, Br, Cl, F, I and an alkoxy group having 1-6 carbon atoms when $R_1$ is H; and wherein $R_1$ is H and at the 4-5 position a benzo group, and a non-toxic, pharmaceutically-acceptable carrier.

7. The method of claim 6 wherein said fungal organism is *Candida albicans*.

8. The method of claim 6 wherein said fungal organism is *Crytococcus neoformans*.

9. The method of claim 6 wherein said fungal organism as *Aspergillus fumigatus*.

10. The compound 4-Bromosampangine.

11. The compound 4-Methoxysampangine.

12. The compound 3-Methoxysampangine.

13. The composition of claim 1 wherein said compound is 4,5-benzosampangine.

14. The method of claim 6 wherein said compound is 4,5-benzosampangine.

15. The compound 4,5-benzosampangine.

* * * * *